(12) United States Patent
De Nanteuil et al.

(10) Patent No.: US 7,498,330 B2
(45) Date of Patent: Mar. 3, 2009

(54) 4-OXO-4,6,7,8-TETRAHYDRO-PYRROLO[1,2-A]PYRAZINE-6-CARBOXAMIDE COMPOUNDS

(75) Inventors: Guillaume De Nanteuil, Suresnes (FR); Philippe Gloanec, Marly le Roi (FR); Jean-Gilles Parmentier, Issy les Moulineaux (FR); Alain Benoist, Franconville (FR); Alain Rupin, Savonnieres (FR); Marie-Odile Vallez, Montreuil (FR); Tony Verbeuren, Verno Uillet (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 589 days.

(21) Appl. No.: 11/079,638

(22) Filed: Mar. 14, 2005

(65) Prior Publication Data

US 2005/0209234 A1   Sep. 22, 2005

(30) Foreign Application Priority Data

Mar. 19, 2004   (FR) .................................. 04 02841

(51) Int. Cl.
*A01N 43/66*  (2006.01)
*A61K 31/53*  (2006.01)
*C07D 241/36*  (2006.01)

(52) U.S. Cl. ....................... 514/241; 544/356
(58) Field of Classification Search ................. 514/241
See application file for complete search history.

(56) References Cited

U.S. PATENT DOCUMENTS 6,156,540 A * 12/2000 Rosen et al. ............... 435/69.2
6,277,851 B1   8/2001 De Nanteuil et al.
6,686,358 B2 * 2/2004 De Nanteuil et al. ........ 514/249

FOREIGN PATENT DOCUMENTS

| EP | 0672658 | 9/1995 |
|---|---|---|
| EP | 1069132 | 1/2001 |
| EP | 1215213 | 6/2002 |
| WO | WO 97/30708 | 8/1997 |
| WO | WO 00/75134 | 12/2000 |

OTHER PUBLICATIONS

Dorwald, F. A. Side Reactions in Organic Synthesis, 2005, Wiley: VCH, Weinheim, p. IX of Preface.*

European Search Report for European Application No. EP 05290599, Sep. 15, 2005.
Nutescu, et al., *Cardiol Clin*, 2008, 26, 169-187.
Abrams, et al., *P&T*, 2007, 32, 271-275.
Reilly, et al., *Blood Coagulation and Fibrinolysis*, 1992, 3, 513-517.

* cited by examiner

*Primary Examiner*—James O Wilson
*Assistant Examiner*—Jeffrey H Murray
(74) *Attorney, Agent, or Firm*—Hueschen and Sage

(57) ABSTRACT

Compound of formula (I):

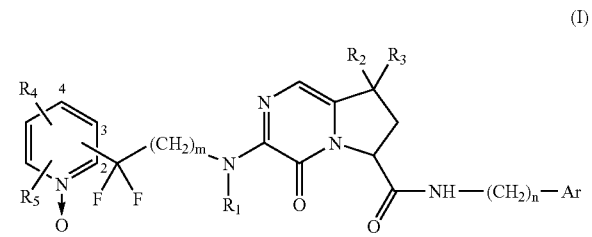

wherein:

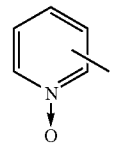

represents 1-oxidopyridyl substituted by the remainder of the molecule in any one of the positions 2, 3 and 4, m and n, which may be identical or different, each represent an integer of from 1 to 3, $R_1$ represents hydrogen or alkyl, $R_2$ and $R_3$, which may be identical or different, each represent an atom or group selected from hydrogen, halogen, alkyl, hydroxy, acyloxy and alkoxy, or, together with the carbon atom carrying them, form a cycloalkane having from 3 to 6 carbon atoms, $R_4$ and $R_5$ each represent hydrogen, or are adjacent and, together with the carbon atoms carrying them, form a benzo ring, Ar represents aryl or heteroaryl.

Medicinal products containing the same which are useful as thrombin inhibitors.

12 Claims, No Drawings

4-OXO-4,6,7,8-TETRAHYDRO-PYRROLO[1,2-A]PYRAZINE-6-CARBOXAMIDE COMPOUNDS

The present invention relates to 4-oxo-4,6,7,8-tetrahydro-pyrrolo[1,2-a]pyrazine-6-carboxamide compounds.

BACKGROUND OF THE INVENTION

Thrombin is the key enzyme for coagulation and plays a central role in the pathology of venous and arterial thromboses, especially in view of its marked ability to cause auto-amplification of the coagulation cascade (F. Toti et al., Sang, Thrombose, Vaisseaux 1992, 4, 483-494 and T. M. Reilly et al., Blood Coagulation and Fibrinolysis 1992, 3, 513-517).

The direct and specific inhibition of thrombin is more efficient and poses fewer risks of haemorrhage than treatment with heparin. Direct inhibitors of thrombin currently exist but the disadvantage of those peptide substances is that they are not active when administered by the oral route.

DESCRIPTION OF THE PRIOR ART

Peptidomimetic compounds having an oral antithrombotic activity have already been described in the literature. They include, for example, the boronic acid compounds described in Patent Specifications EP 293 881, EP 471 651, EP 615 978 and EP 792 883 and the compounds described in Patent Specifications WO 94 29336, WO 95 23609 and EP 1 069 132.

DETAILED DESCRIPTION OF THE INVENTION

The problem of the present invention was to obtain new thrombin inhibitors active by the oral route that are simultaneously well absorbed, potent, selective and reliable in use. In that respect, it is important to have compounds that present little risk of interaction with food or medicaments.

More specifically, the present invention relates to compounds of formula (I):

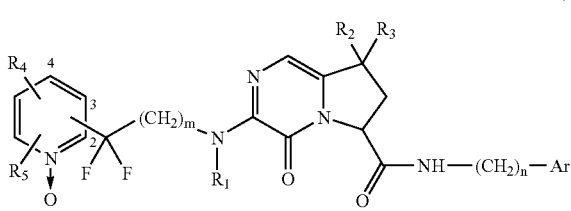

wherein:

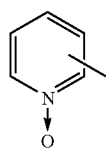

represents a 1-oxidopyridyl group substituted by the remainder of the molecule in any one of the positions 2, 3 and 4, m and n, which may be identical or different, each represent an integer of from 1 to 3, $R_1$ represents a hydrogen atom or a linear or branched ($C_1$-$C_6$)alkyl group, $R_2$ and $R_3$, which may be identical or different, each represent an atom or group selected from the atoms hydrogen and halogen and the groups linear or branched ($C_1$-$C_6$)alkyl, hydroxy, linear or branched ($C_1$-$C_6$)acyloxy and linear or branched ($C_1$-$C_6$)alkoxy, or together form, with the carbon atom carrying them, a cycloalkane having from 3 to 6 carbon atoms, $R_4$ and $R_5$ each represent a hydrogen atom, or are adjacent and together form, with the carbon atoms carrying them, a benzo ring, Ar represents an aryl or heteroaryl group, to their enantiomers, and to addition salts thereof with a pharmaceutically acceptable acid.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid, etc.

"Aryl group" is understood to mean phenyl, biphenylyl or naphthyl, each of those groups being optionally substituted by one or more identical or different groups selected from:
halogen,
linear or branched ($C_1$-$C_6$)alkyl optionally substituted by a hydroxy, carboxy or carbamoyl group, the carbamoyl group being itself optionally substituted by one or two linear or branched ($C_1$-$C_6$)alkyl groups,
linear or branched ($C_1$-$C_6$)alkoxy,
hydroxy,
trihalo-($C_1$-$C_6$)alkyl in which the alkyl moiety may be linear or branched,
amino optionally substituted by one or two linear or branched ($C_1$-$C_6$)alkyl groups,
carboxymethoxy,
and carbamoylmethoxy optionally N-substituted by one or two groups selected from linear or branched ($C_1$-$C_6$) alkyl, hydroxy-($C_1$-$C_6$)alkyl in which the alkyl moiety may be linear or branched, alkoxyalkyl group in which the alkoxy and alkyl moieties are each linear or branched $C_1$-$C_6$, and pyridylalkyl in which the alkyl moiety is linear or branched $C_1$-$C_6$.

"Heteroaryl group" is understood to mean a mono- or bi-cyclic aromatic group having from 5 to 12 ring members and containing one, two or three hetero atoms selected from oxygen, nitrogen and sulphur, it being understood that the heteroaryl may be optionally substituted by one or more identical or different groups selected from:
halogen,
linear or branched ($C_1$-$C_6$)alkyl optionally substituted by a hydroxy, carboxy or carbamoyl group, the carbamoyl group being itself optionally substituted by one or two linear or branched ($C_1$-$C_6$)alkyl groups,
hydroxy,
oxo,
linear or branched ($C_1$-$C_6$)alkoxy,
trihalo-($C_1$-$C_6$)alkyl in which the alkyl moiety may be linear or branched,
amino optionally N-substituted by one or two linear or branched ($C_1$-$C_6$)alkyl groups, carboxymethoxy, and carbamoylmethoxy optionally N-substituted by one or two groups selected from linear or branched ($C_1$-$C_6$) alkyl, hydroxy-($C_1$-$C_6$)alkyl in which the alkyl moiety may be linear or branched, alkoxyalkyl in which the alkoxy and alkyl moieties are each linear or branched $C_1$-$C_6$, and pyridylalkyl in which the alkyl moiety is linear or branched $C_1$-$C_6$.

Among the heteroaryl groups there may be mentioned, without implying any limitation, the groups thienyl, pyridyl, furyl, pyrrolyl, imidazolyl, oxazolyl, isoxazolyl, thiazolyl, isothiazolyl, pyrimidinyl, pyrazinyl, pyridazinyl, indolyl, benzofuryl and quinolyl.

m is preferably 1.

n is preferably 1.

$R_1$, $R_2$ and $R_3$ each preferably represent a hydrogen atom.

An advantageous embodiment of the invention relates to compounds of formula (I) wherein $R_4$ and $R_5$ each represent a hydrogen atom.

Another advantageous embodiment of the invention relates to compounds of formula (I) wherein $R_4$ and $R_5$ are adjacent and together form, with the carbon atoms carrying them, a benzo ring.

The group Ar is preferably a phenyl, thienyl or pyridyl group, each of those groups being unsubstituted or substituted by one or more identical or different groups selected from:

halogen, linear or branched ($C_1$-$C_6$)alkyl optionally substituted by a hydroxy, carboxy or carbamoyl group, the carbamoyl group being itself optionally substituted by one or two linear or branched ($C_1$-$C_6$)alkyl groups, linear or branched ($C_1$-$C_6$)alkoxy, hydroxy, trihalo-($C_1$-$C_6$)alkyl in which the alkyl moiety may be linear or branched, amino optionally substituted by one or two linear or branched ($C_1$-$C_6$)alkyl groups, carboxymethoxy, and carbamoylmethoxy optionally N-substituted by one or two groups selected from linear or branched ($C_1$-$C_6$) alkyl, hydroxy-($C_1$-$C_6$)alkyl in which the alkyl moiety may be linear or branched, alkoxyalkyl in which the alkoxy and alkyl moieties are each linear or branched $C_1$-$C_6$, and pyridylalkyl in which the alkyl moiety is linear or branched $C_1$-$C_6$.

More preferably, Ar represents a phenyl group unsubstituted or substituted by one or more identical or different halogen atoms selected from fluorine and chlorine.

Preferred compounds of formula (I) are

3-{[2,2-difluoro-2-(1-oxido-2-pyridyl)ethyl]amino}-N-(2-fluorobenzyl)-4-oxo-4,6,7,8-tetrahydropyrrolo[1,2-a]pyrazine-6-carboxamide, and its (6S) enantiomer;

3-{[2,2-difluoro-2-(1-oxido-2-pyridyl)ethyl]amino}-N-(2,6-difluorobenzyl)-4-oxo-4,6,7,8-tetrahydropyrrolo[1,2-a]pyrazine-6-carboxamide, and its (6S) enantiomer;

3-{[2,2-difluoro-2-(1-oxido-2-pyridyl)ethyl]amino}-N-(2-chlorobenzyl)-4-oxo-4,6,7,8-tetrahydropyrrolo[1,2-a]pyrazine-6-carboxamide, and its (6S) enantiomer;

3-{[2,2-difluoro-2-(1-oxido-2-pyridyl)ethyl]amino}-N-(2,5-difluorobenzyl)-4-oxo-4,6,7,8-tetrahydropyrrolo[1,2-a]pyrazine-6-carboxamide, and its (6S) enantiomer;

3-{[2,2-difluoro-2-(1-oxido-2-pyridyl)ethyl]amino}-N-(2,3-difluorobenzyl)-4-oxo-4,6,7,8-tetrahydropyrrolo[1,2-a]pyrazine-6-carboxamide, and its (6S) enantiomer, and 3-{[2,2-difluoro-2-(1-oxido-2-pyridyl)ethyl]amino}-N-(2,3,6-trifluorobenzyl)-4-oxo-4,6,7,8-tetrahydropyrrolo[1,2-a]pyrazine-6-carboxamide, and its (6S) enantiomer.

The invention relates also to a process for the preparation of compounds of formula (I) which is characterised in that a compound of formula (II):

wherein $R_2$ and $R_3$ are as defined for formula (I), $P_1$ represents a protecting group for the amino function and Bn represents a benzyl group is reduced, using a reducing agent, to yield a compound of formula (III):

wherein $R_2$, $R_3$, $P_1$ and Bn are as defined hereinbefore, the hydroxy function of which is converted to methoxy and then to the cyano function by conventional reactions of organic chemistry to yield, after deprotection of the amino function, a compound of formula (IV):

wherein $R_2$, $R_3$ and Bn are as defined hereinbefore, which is reacted with oxalyl chloride to yield a compound of formula (V):

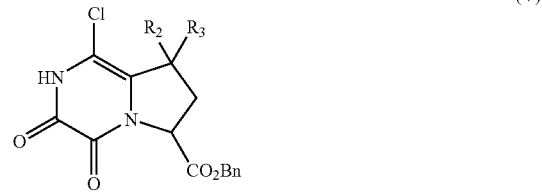

wherein $R_2$, $R_3$ and Bn are as defined hereinbefore, which is subjected to catalytic hydrogenation to yield a compound of formula (VI):

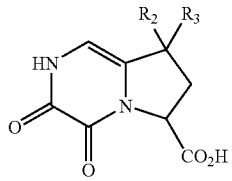
(VI)

wherein $R_2$ and $R_3$ are as defined hereinbefore, which is esterified to form a compound of formula (VII):

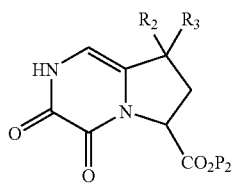
(VII)

wherein $R_2$ and $R_3$ are as defined hereinbefore and $P_2$ represents a linear or branched $(C_1-C_6)$alkyl group, which is reacted with a brominating agent to yield a compound of formula (VIII):

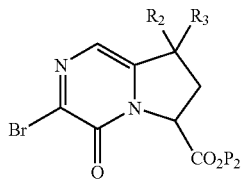
(VIII)

wherein $R_2$, $R_3$ and $P_2$ are as defined hereinbefore, which is reacted with 2-mercaptopyridine to yield a compound of formula (IX):

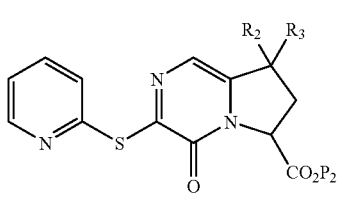
(IX)

wherein $R_2$, $R_3$ and $P_2$ are as defined hereinbefore, which is reacted with an N-oxide of formula (X):

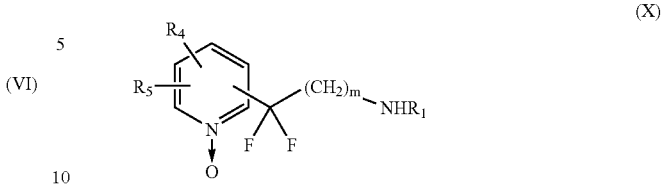
(X)

wherein m, $R_1$, $R_4$ and $R_5$ are as defined for formula (I), to yield a compound of formula (XI)

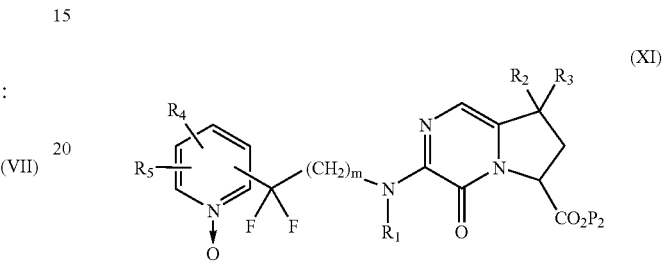
(XI)

wherein m, $R_1$, $R_2$, $R_3$, $R_4$, $R_5$ and $P_2$ are as defined hereinbefore, the acid function of which is deprotected to yield a compound of formula (XII)

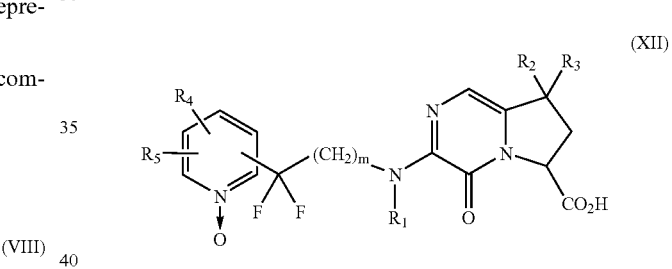
(XII)

wherein m, $R_1$, $R_2$, $R_3$, $R_4$ and $R_5$ are as defined hereinbefore, which is reacted with a compound of formula (XIII):

$H_2N-[CH_2]_n-Ar$ (XIII)

wherein n and Ar are as defined for formula (I), in the presence of a coupling agent, to yield a compound of formula (I).

The addition salts of the compounds of formula (I) are obtained by reaction of the compound with a pharmaceutically acceptable acid.

The compounds of formula (I) have an asymmetric centre and are therefore capable of existing in the form of a racemic mixture or in optically active form.

The optically active compounds of formula (I) can be obtained, for example, by using a corresponding optically active compound of formula (II) as starting material or by separation of the corresponding racemic mixture of formula (I), for example by chiral HPLC chromatography.

Preferred compounds of formula (I) are those wherein the configuration of the asymmetric centre in the alpha position with respect to the amide is (S).

The compounds of formula (II) are obtained by benzylation of the corresponding acids.

The compounds of the present invention have especially valuable pharmacological properties.

They are potent inhibitors of thrombin which are active by the oral route.

Those properties render them useful in the treatment of stable or unstable angina, disorders of thrombotic origin and/or giving rise to thrombotic complications, in the treatment or prevention of myocardial infarction and venous or arterial thromboses, and in the treatment of complications of vascular and cardiovascular diseases such as atherosclerosis, arteritis, venous disease, and in the treatment of any disorders involving thrombin formation and/or activity.

They may also be used in therapeutic association with a thrombolytic.

The invention relates also to pharmaceutical compositions comprising as active ingredient a compound of formula (I) together with one or more suitable inert, non-toxic excipients. Among the pharmaceutical compositions according to the invention there may be mentioned more especially those which are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions, etc.

The useful dosage can be adapted according to the nature and severity of the disorder, the route of administration and the age and weight of the patient. The dosage varies from 1 to 500 mg per day in one or more administrations.

The following Examples illustrate the invention.

The starting materials employed are known products or are prepared according to known procedures.

The structures of the compounds described in the Examples were determined according to customary spectrophotometric techniques (infra-red NMR, mass spectrometry).

EXAMPLE 1

3-{[2,2-Difluoro-2-(1-oxido-2-pyridyl)ethyl]amino}-N-(2-fluorobenzyl)$_4$-oxo-4,6,7,8-tetrahydropyrrolo[1,2-a]pyrazine-6-carboxamide Step A: Benzyl N-tert-butoxycarbonyl-5-oxoprolinate At 0° C., 11 mmol of dimethylaminopyridine and 11 mmol of di-tert-butyl dicarbonate are added to 10 mmol of benzyl 5-oxoprolinate (the preparation process for which is described by E. Campaigne et al. (J. Heterocycl. Chem. 1975, 12, 391)) in solution in dichloromethane. After stirring for 24 hours at ambient temperature, the reaction mixture is washed and then dried and evaporated to yield the expected product in the form of a viscous oil.

Step B: Benzyl N-tert-butoxycarbonyl-5-hydroxyprolinate

Under argon and at −78° C., 18 mmol of a 1M solution of diisobutylaluminium hydride in hexane are added to 10 mmol of the compound obtained in the above Step in solution in tetrahydrofuran. After stirring for 20 minutes at −78° C., a saturated aqueous solution of ammonium chloride is added, followed by an aqueous 10% sodium carbonate solution. After stirring overnight at ambient temperature, the reaction mixture is filtered and the filtrate is evaporated and taken up in dichloromethane. The organic phase is washed, dried and then evaporated. The residue is purified by chromatography on silica gel, using a 95/5 dichloromethane/ethyl acetate mixture as eluant. The expected product is obtained in the form of a yellow oil.

Step C: Benzyl N-tert-butoxycarbonyl-5-methoxyprolinate

A 0.1% solution of para-toluenesulphonic acid in anhydrous methanol (88 ml) is added to 10 mmol of the compound obtained in the above Step. After stirring for ½ hour, an aqueous 10% sodium carbonate solution is added and the product is extracted with dichloromethane. The expected product is obtained in the form of a slightly yellow oil.

Step D: Benzyl 5-cyanoprolinate hydrochloride

At −40° C. and under argon, a 5% v/v solution of tin tetrachloride in anhydrous dichloromethane (7.1 ml), and then trimethylsilyl cyanide (20.6 mmol), are added to 10 mmol of the compound obtained in the above Step. After stirring for 2 hours at 40° C., an aqueous 10% sodium carbonate solution is added, the aqueous phase is extracted with dichloromethane, and the organic phase is washed, dried and then evaporated. The residue obtained is purified by chromatography on silica gel using a 95/5 dichloromethane/ethyl acetate mixture as eluant. The yellow oil obtained is dissolved in ethyl acetate and then a stream of HCl gas is passed through for 30 minutes at 0° C. After stirring overnight at ambient temperature, the precipitate formed is filtered off, rinsed with ethyl acetate and dried in vacuo using a dessicator.

Step E: Benzyl 1-chloro-3,4-dioxo-2,3,4,6,7,8-hexahydropyrrolo[1,2-a]pyrazine-6-carboxylate At 0° C., oxalyl chloride (144 ml) is added to 200 g of the compound obtained in the above Step in solution in toluene. The mixture is then brought to ambient temperature and stirred for 15 hours, and the solvent is subsequently evaporated off. The residue obtained is purified by chromatography on silica, using a 9/1 dichloromethane/methanol mixture as eluant, to yield the expected product.

Step F: 3,4-Dioxo-2,3,4,6,7,8-hexahydropyrrolo[1,2-a]pyrazine-6-carboxylic acid 3 g of the compound obtained in the above Step are dissolved in 50 ml of ethanol and then 1.43 ml of triethylamine are added, followed by 0.5 g of palladium-on-carbon. The mixture is then placed under a hydrogen atmosphere at ambient temperature and atmospheric pressure for 5 hours. After removal of the catalyst by filtration, the solvent is evaporated off to yield the expected product.

Step G: Ethyl 3,4-dioxo-2,3,4,6,7,8-hexahydropyrrolo[1,2-a]pyrazine-6-carboxylate 11.83 ml of trimethylsilyl chloride are added dropwise, at 0° C., to a suspension of 1.83 g of the compound obtained in the above Step in 20 ml of anhydrous ethanol. The reaction mixture is then stirred at ambient temperature for 15 hours. The solvent is evaporated off and the residue is taken up in dichloromethane. The organic phase is washed, dried, filtered and evaporated, and then the crude product is purified by chromatography on silica (eluant: dichloromethane/ethanol 95/5) to yield the expected product.

Step H: Ethyl 3-bromo-4-oxo-4,6,7,8-tetrahydropyrrolo[1,2-a]pyrazine-6-carboxylate 34.7 g of dibasic sodium phosphate ($Na_2HPO_4$) in 90 ml of dichloroethane, and then 100 g of phosphorus oxybromide ($POBr_3$) in 340 ml of dichloroethane, are added to 73 g of the compound obtained in the above Step suspended in 400 ml of dichloroethane. The reaction mixture is then heated at 50° C. for 16 hours, subsequently cooled to 0° C. using a bath of water and ice, and 650 ml of a 10% sodium carbonate solution are added.

The organic phase is washed with water, then the aqueous phases are combined and extracted with isopropyl acetate. The combined organic phases are concentrated to 160 ml, and then 160 ml of isopropyl acetate are added and the mixture is again concentrated to 160 ml. The mixture is subsequently placed in a bath at 50° C. and 250 ml of n-heptane are added in the course of 1 hours. After a further hour at 50° C., the precipitate obtained is filtered off, rinsed with a 1/3 mixture of isopropyl acetate and n-heptane, and dried to yield the expected product.

Step I: Ethyl 4-oxo-3-(2-pyridylthio)-4,6,7,8-tetrahydropyrrolo[1,2-a]pyrazine-6-carboxylate 34.3 g of 2-mercaptopyridine are added in three batches, at 20 minute intervals, to 80.5 g of the compound obtained in the above Step in solution in 410 ml of acetonitrile. The addition is exothermic and the temperature of the reaction mixture rises to 35° C.

The mixture becomes heterogeneous. After stirring for 1 hour 45 minutes, the solvent is evaporated off and the residue is taken up in ethyl acetate and in water. The organic phase is washed, dried, filtered and evaporated to dryness. The residue obtained is purified on a chromatography column (dichloromethane/ethanol 98/2 then 95/5) to yield the expected product in the form of an orange oil which slowly crystallises.

Step J: Ethyl 3-{[2,2-difluoro-2-(1-oxido-2-pyridyl)ethyl]amino}-4-oxo-4,6,7,8-tetrahydropyrrolo[1,2-a]pyrazine-6-carboxylate 2.78 g of 2,2-difluoro-2-(1-oxido-2-pyridyl)ethanamine, and then 1.5 g zinc chloride, are added to 4.6 g of the compound obtained in the above Step suspended in 30 ml of acetonitrile. The mixture is then heated at reflux for 15 hours. The reaction mixture becomes clear. The solvent is then evaporated off and the residue is taken up in dichloromethane. The organic phase is washed, dried, filtered and evaporated, and the residue obtained is purified by chromatography on silica (eluant: dichloromethane/isopropanol 9/1) to yield the expected product.

Step K: 3-{[2,2-Difluoro-2-(1-oxido-2-pyridyl)ethyl]amino}-4-oxo-4,6,7,8-tetrahydropyrrolo[1,2-a]pyrazine-6-carboxylic acid 2 equivalents of 1N sodium hydroxide solution are added to 9 g of the compound obtained in the above Step in solution in 100 ml of dioxane and 20 ml of water. After 24 hours at ambient temperature, acidification is carried out using 2 equivalents of 1N hydrochloric acid, and then the reaction mixture is evaporated. The residue is taken up twice in 30 ml of toluene and dried, yielding the expected product in the form of a white solid.

Step L: 3-{[2,2-Difluoro-2-(1-oxido-2-pyridyl)ethyl]amino}-N-(2-fluorobenzyl)-4-oxo-4,6,7,8-tetrahydropyrrolo[1,2-a]pyrazine-6-carboxamide 3 g of the compound obtained in the above Step are reacted with 1.18 g of 2-fluorobenzylamine in the presence of 3.57 g of 1-[bis(dimethylamino)methylene]-1H-1,2,3-triazolo[4,5-b]pyridinium 3-oxide hexafluorophosphate (HATU) and 1.64 ml of diisopropylethylamine in 60 ml of dimethylformamide.

After stirring for 15 hours at ambient temperature, the solvent is evaporated off and the residue obtained is taken up in ethyl acetate and in water. The organic phase is washed, dried and then evaporated, and the residue is purified by chromatography on silica to yield the expected product in the form of a racemic mixture.

Elemental microanalysis:

|  | % C | % H | % N |
| --- | --- | --- | --- |
| Calculated: | 57.52 | 4.39 | 15.24 |
| Found: | 57.63 | 4.18 | 15.05 |

EXAMPLE 2

(6R)-3-{[2,2-Difluoro-2-(1-oxido-2-pyridyl)ethyl]amino}-N-(2-fluorobenzyl)-4-oxo-4,6,7,8-tetrahydropyrrolo[1,2-a]pyrazine-6-carboxamide The racemic mixture of Example 1 is separated by chiral phase preparative HPLC chromatography (Chiralpak AD column, eluant: acetonitrile/isopropanol/diethylamine 500/500/1).

The expected product is the first of the enantiomers so obtained.

EXAMPLE 3

(6S)-3-{[2,2-Difluoro-2-(1-oxido-2-pyridyl)ethyl]amino}-N-(2-fluorobenzyl)-4-oxo-4,6,7,8-tetrahydropyrrolo[1,2-a]pyrazine-6-carboxamide The racemic mixture of Example 1 is separated by chiral phase preparative HPLC chromatography (Chiralpak AD column, eluant: acetonitrile/isopropanol/diethylamine 500/500/1).

The expected product is the second of the enantiomers so obtained.

Index of rotation: $\alpha_D = -116.07°$ (methanol, 20° C., c=1.4)

EXAMPLE 4

(6R)-3-{[2,2-Difluoro-2-(1-oxido-2-pyridyl)ethyl]amino}-N-{2-[2-(ethylamino)-2-oxoethoxy]benzyl}-4-oxo-4,6,7,8-tetrahydropyrrolo[1,2-a]pyrazine-6-carboxamide The expected product is obtained according to the procedure described in Example 1, with the replacement of 2-fluorobenzylamine with 2-[2-(aminomethyl)phenoxy]-N-ethylacetamide in Step L, followed by separation of the racemic mixture so obtained by preparative chiral HPLC chromatography (Chiralpak AD column, eluant acetonitrile/isopropanol/diethylamine 500/500/1).

The expected product is the first of the enantiomers so obtained.

Elemental Microanalysis:

|            | % C   | % H  | % N   |
|------------|-------|------|-------|
| Calculated: | 57.56 | 5.20 | 15.49 |
| Found:      | 58.11 | 5.15 | 15.55 |

Index of rotation: $\alpha_D$=+93.1°(methanol, 20° C., c=0.7)

EXAMPLE 5

(6S)-3-{[2,2-Difluoro-2-(1-oxido-2-pyridyl)ethyl]amino}-N-{2-[2-(ethylamino)-2-oxoethoxy]benzyl}4-oxo-4,6,7,8-tetrahydropyrrolo[1,2-a]pyrazine-6-carboxamide The expected product is the second of the enantiomers separated in Example 4.

Index of rotation: $\alpha_D$=−98.8°(methanol, 20° C., c=0.8)

EXAMPLE 6

3-{[2,2-Difluoro-2-(1-oxido-2-pyridyl)ethyl]amino}-N-(2,4-difluorobenzyl)$_4$-oxo-4,6,7,8-tetrahydropyrrolo[1,2-a]pyrazine-6-carboxamide The expected product is obtained according to the procedure described in Example 1, with the replacement of 2-fluorobenzylamine with 2,4-difluorobenzylamine in Step L.

Mass spectrometry ESI (acetonitrile/water): [M+H]+ =478.15.

EXAMPLE 7

3-{[2,2-Difluoro-2-(1-oxido-2-pyridyl)ethyl]amino}-N-(2,6-difluorobenzyl)$_4$-oxo-4,6,7,8-tetrahydropyrrolo[1,2-a]pyrazine-6-carboxamide The expected product is obtained according to the procedure described in Example 1, with the replacement of 2-fluorobenzylamine with 2,6-difluorobenzylamine in Step L.

Melting point: 227-228° C.

Elemental microanalysis:

|            | % C   | % H  | % N   |
|------------|-------|------|-------|
| Calculated: | 55.35 | 4.01 | 14.67 |
| Found:      | 55.04 | 4.04 | 14.28 |

EXAMPLE 8

3-{[2,2-Difluoro-2-(1-oxido-2-pyridyl)ethyl]amino}-N-(2-chlorobenzyl)-4-oxo-4,6,7,8-tetrahydropyrrolo[1,2-a]pyrazine-6-carboxamide The expected product is obtained according to the procedure described in Example 1, with the replacement of 2-fluorobenzylamine with 2-chlorobenzylamine in Step L.

Elemental microanalysis:

|            | % C   | % H  | % N   | % Cl |
|------------|-------|------|-------|------|
| Calculated: | 55.53 | 4.24 | 14.72 | 7.45 |
| Found:      | 55.32 | 4.33 | 14.33 | 7.73 |

EXAMPLE 9

3-{[2,2-Difluoro-2-(1-oxido-2-pyridyl)ethyl]amino}-N-(3,4-difluorobenzyl)-4-oxo-4,6,7,8-tetrahydropyrrolo[1,2-a]pyrazine-6-carboxamide The expected product is obtained according to the procedure described in Example 1, with the replacement of 2-fluorobenzylamine with 3,4-difluorobenzylamine in Step L.

Melting point: 204° C.

Elemental microanalysis:

|            | % C   | % H  | % N   |
|------------|-------|------|-------|
| Calculated: | 55.35 | 4.01 | 14.67 |
| Found:      | 55.07 | 3.92 | 14.40 |

EXAMPLE 10

3-{[2,2-Difluoro-2-(1-oxido-2-pyridyl)ethyl]amino}-N-(2,5-difluorobenzyl)-4-oxo-4,6,7,8-tetrahydropyrrolo[1,2-a]pyrazine-6-carboxamide The expected product is obtained according to the procedure described in Example 1, with the replacement of 2-fluorobenzylamine with 2,5-difluorobenzylamine in Step L.

Melting point: 189° C.

Elemental microanalysis:

|            | % C   | % H  | % N   |
|------------|-------|------|-------|
| Calculated: | 55.35 | 4.01 | 14.67 |
| Found:      | 55.95 | 4.41 | 14.13 |

EXAMPLE 11

3-{[2,2-Difluoro-2-(1-oxido-2-pyridyl)ethyl]amino}-N-(2,6-dichlorobenzyl)$_4$-oxo-4,6,7,8-tetrahydropyrrolo[1,2-a]pyrazine-6-carboxamide The expected product is obtained according to the procedure described in Example 1, with the replacement of 2-fluorobenzylamine with 2,6-dichlorobenzylamine in Step L.

Melting point: 122° C.

Elemental microanalysis

|            | % C   | % H  | % N   | % Cl  |
|------------|-------|------|-------|-------|
| Calculated: | 51.78 | 3.75 | 13.72 | 13.89 |
| Found:      | 52.23 | 3.73 | 13.66 | 14.06 |

EXAMPLE 12

3-{[2,2-Difluoro-2-(1-oxido-2-pyridyl)ethyl]amino}-N-(2-chloro-6-fluorobenzyl)-4-oxo-4,6,7,8-tetrahydropyrrolo[1,2-a]pyrazine-6-carboxamide The expected product is obtained according to the procedure described in Example 1, with the replacement of 2-fluorobenzylamine with 2-chloro-6-fluorobenzylamine in Step L.

Melting point: 221° C.

Elemental microanalysis:

|  | % C | % H | % N | % Cl |
|---|---|---|---|---|
| Calculated: | 53.50 | 3.88 | 14.18 | 7.18 |
| Found: | 53.93 | 3.97 | 14.06 | 7.28 |

EXAMPLE 13

3-{[2,2-Difluoro-2-(1-oxido-2-pyridyl)ethyl]amino}-N-(2,3-difluorobenzyl)-4-oxo-4,6,7,8-tetrahydropyrrolo[1,2-a]pyrazine-6-carboxamide The expected product is obtained according to the procedure described in Example 1, with the replacement of 2-fluorobenzylamine with 2,3-difluorobenzylamine in Step L.

Melting point: 142° C.

Elemental microanalysis:

|  | % C | % H | % N |
|---|---|---|---|
| Calculated: | 55.35 | 4.01 | 14.67 |
| Found: | 55.34 | 4.26 | 14.42 |

EXAMPLE 14

3-{[2,2-Difluoro-2-(1-oxido-2-pyridyl)ethyl]amino}-N-(3,5-difluorobenzyl)-4-oxo-4,6,7,8-tetrahydropyrrolo[1,2-a]pyrazine-α-carboxamide The expected product is obtained according to the procedure described in Example 1, with the replacement of 2-fluorobenzylamine with 3,5-difluorobenzylamine in Step L.

Melting point: 218-219° C.

Elemental microanalysis:

|  | % C | % H | % N |
|---|---|---|---|
| Calculated: | 55.35 | 4.01 | 14.67 |
| Found: | 54.72 | 3.82 | 14.40 |

EXAMPLE 15

3-{[2,2-Difluoro-2-(1-oxido-2-pyridyl)ethyl]amino}4-oxo-N-[2-(2-oxo-2-{[2-(2-pyridyl)ethyl]amino}ethoxy)benzyl]-4,6,7,8-tetrahydropyrrolo[1,2-a]pyrazine-6-carboxamide hydrochloride Step A: 3-{[2,2-Difluoro-2-(1-oxido-2-pyridyl)ethyl]amino}-4-oxo-N-[2-(2-oxo-2-{[2-(2-pyridyl)ethyl]amino}ethoxy)benzyl]-4,6,7,8-tetrahydropyrrolo[1,2-a]pyrazine-6-carboxamide The expected product is obtained according to the procedure described in Example 1, with the replacement of 2-fluorobenzylamine with 2-[2-(aminomethyl)phenoxy]-N-[2-(2-pyridyl)ethyl]acetamide in Step L.

Step B: 3-{[2,2-Difluoro-2-(1-oxido-2-pyridyl)ethyl]amino}-4-oxo-N-[2-(2-oxo-2-{[2-(2-pyridyl)ethyl]amino}ethoxy)benzyl]-4,6,7,8-tetrahydropyrrolo[1,2-a]pyrazine-6-carboxamide hydrochloride The expected product is obtained by acidification of the compound obtained in the above Step using hydrochloric acid.

Elemental microanalysis:

|  | % C | % H | % N | % Cl |
|---|---|---|---|---|
| Calculated: | 56.75 | 4.92 | 14.94 | 5.40 |
| Found: | 57.22 | 4.85 | 14.87 | 5.82 |

EXAMPLE 16

(6S)-3-{[2,2-Difluoro-2-(1-oxido-2-pyridyl)ethyl]amino}-N-(2,6-difluorobenzyl)4-oxo-4,6,7,8-tetrahydropyrrolo[1,2-a]pyrazine-6-carboxamide The expected product is obtained by separation of the racemic mixture of Example 7 on a chiral HPLC column.

Index of rotation: $\alpha_D = -118.46°$ (methanol, 20° C., c=0.95)

EXAMPLE 17

(6S)-3-{[2,2-Difluoro-2-(1-oxido-2-pyridyl)ethyl]amino}-N-(2,5-difluorobenzyl)-4-oxo-4,6,7,8-tetrahydropyrrolo[1,2-a]pyrazine-6-carboxamide The expected product is obtained by separation of the racemic mixture of Example 10 on a chiral HPLC column.

Index of rotation: $\alpha_D = -89.65$ (methanol, 20° C., c=0.57)

EXAMPLE 18

(6S)-3-{[2,2-Difluoro-2-(1-oxido-2-pyridyl)ethyl]amino}-N-(2-chloro-6-fluorobenzyl)$_4$-oxo-4,6,7,8-tetrahydropyrrolo[1,2-a]pyrazine-6-carboxamide The expected product is obtained by separation of the racemic mixture of Example 12 on a chiral HPLC column.

Index of rotation: $\alpha_D = -101.49°$ (methanol, 20° C., c=1.3)

EXAMPLE 19

(6S)-3-{[2,2-Difluoro-2-(1-oxido-2-pyridyl)ethyl]amino}-N-(2,3-difluorobenzyl)-4-oxo-4,6,7,8-tetrahydropyrrolo[1,2-a]pyrazine-6-carboxamide The expected product is obtained by separation of the racemic mixture of Example 13 on a chiral HPLC column.

Index of rotation: $\alpha_D = -102.06$ (methanol, 20° C., c=0.8)

EXAMPLE 20

(6S)-3-{[2,2-Difluoro-2-(1-oxido-2-pyridyl)ethyl]amino}-N-(2-chlorobenzyl)-4-oxo-4,6,7,8-tetrahydropyrrolo[1,2-a]pyrazine-6-carboxamide The expected product is obtained by separation of the racemic mixture of Example 8 on a chiral HPLC column.

Index of rotation: $\alpha_D = -105.65°$ (methanol, 20° C., c=0.85)

EXAMPLE 21

(6S)-3-{[2,2-Difluoro-2-(1-oxido-2-pyridyl)ethyl]amino}-N-(2,3,6-trifluorobenzyl)-4-oxo-4,6,7,8-tetrahydropyrrolo[1,2-a]pyrazine-6-carboxamide Step A: 3-{[2,2-Difluoro-2-(1-oxido-2-pyridyl)ethyl]amino}-N-(2,3,6-trifluorobenzyl)-4-oxo-4, 6, 7, 8-tetrahydropyrrolo[1,2-a]pyrazine-6-carboxamide The expected product is obtained according to the procedure described in Example 1, with the replacement of 2-fluorobenzylamine with 2,3,6-trifluorobenzylamine in Step L.

Step B: (6S)-3-{[2,2-Difluoro-2-(1-oxido-2-pyridyl)ethyl]amino}-N-(2,3,6-trifluorobenzyl)-4-oxo-4,6,7,8-tetrahydropyrrolo[1,2-a]pyrazine-6-carboxamide The expected product is obtained by separation of the racemic mixture obtained in the above Step on a chiral HPLC column.

Index of rotation: $\alpha_D = -118.25$ (methanol, 20° C., c=1)

EXAMPLE 22

(6S)-3-{[2,2-Difluoro-2-(1-oxido-2-pyridyl)ethyl]amino}-N-benzyl-4-oxo-4,6,7,8-tetrahydropyrrolo[1,2-a]pyrazine-6-carboxamide hydrochloride Step A: 3-{[2,2-Difluoro-2-(1-oxido-2-pyridyl)ethyl]amino}-N-benzyl-4-oxo-4,6,7,8-tetrahydropyrrolo[1,2-a]pyrazine-6-carboxamide The expected product is obtained according to the procedure described in Example 1, with the replacement of 2-fluorobenzylamine with benzylamine in Step L.

Step B: (6S)-3-{[2,2-Difluoro-2-(1-oxido-2-pyridyl)ethyl]amino}-N-benzyl-4-oxo-4,6,7,8-tetrahydropyrrolo[1,2-a]pyrazine-6-carboxamide The expected product is obtained by separation of the racemic mixture obtained in the above Step on a chiral HPLC column.

Step C: (6S)-3-{[2,2-Difluoro-2-(1-oxido-2-pyridyl)ethyl]amino}-N-benzyl-4-oxo-4,6,7,8-tetrahydropyrrolo[1,2-a]pyrazine-6-carboxamide hydrochloride The expected product is obtained by acidification of the compound obtained in the above Step using hydrochloric acid.

Elemental microanalysis:

|  | % C | % H | % N | % Cl |
|---|---|---|---|---|
| Calculated: | 55.29 | 4.64 | 14.65 | 7.42 |
| Found: | 54.84 | 4.81 | 14.16 | 7.16 |

EXAMPLE 23

(6S)-3-{[2,2-Difluoro-2-(1-oxido-2-pyridyl)ethyl]amino}-N-(3-thienylmethyl)-4-oxo-4,6,7,8-tetrahydropyrrolo[1,2-a]pyrazine-6-carboxamide hydrochloride The expected product is obtained according to the procedure described in Example 22, with the replacement of benzylamine with 3-thienylmethylamine in Step A.

Elemental microanalysis:

|  | % C | % H | % N | % Cl | % S |
|---|---|---|---|---|---|
| Calculated: | 49.64 | 4.17 | 14.47 | 7.33 | 6.63 |
| Found: | 49.09 | 4.17 | 14.14 | 8.16 | 6.59 |

EXAMPLE 24

(6S)-3-{[2,2-Difluoro-2-(1-oxido-2-pyridyl)ethyl]amino}-N-(2-thienylmethyl)-4-oxo-4,6,7,8-tetrahydropyrrolo[1,2-a]pyrazine-6-carboxamide hydrochloride The expected product is obtained according to the procedure described in Example 22, with the replacement of benzylamine with 2-thienylmethylamine in Step A. Elemental microanalysis:

|  | % C | % H | % N | % Cl | % S |
|---|---|---|---|---|---|
| Calculated: | 49.64 | 4.17 | 14.47 | 7.33 | 6.63 |
| Found: | 50.61 | 4.12 | 14.35 | 7.98 | 6.65 |

EXAMPLE 25

(6S)-3-{[2,2-Difluoro-2-(1-oxido-4-pyridyl)ethyl]amino}-N-(2-fluorobenzyl)-4-oxo-4,6,7,8-tetrahydropyrrolo[1,2-a]pyrazine-6 -carboxamide Step A: 3-{[2,2-Difluoro-2-(1-oxido-4-pyridyl)ethyl]amino}-N-(2-fluorobenzyl)-4-oxo-4,6,7,8-tetrahydropyrrolo[1,2-a]pyrazine-6-carboxamide The expected product is obtained according to the procedure described in Example 1, with the replacement of 2,2- difluoro-2-(1-oxido-2-pyridyl)ethanamine with 2,2-difluoro-2-(1-oxido-4-pyridyl)ethanamine in Step J.

Step B: (6S)-3-{[2,2-Difluoro-2-(1-oxido-4-pyridyl)ethyl]amino}-N-(2-fluorobenzyl)-4-oxo-4,6,7,8-tetrahydropyrrolo[1,2-a]pyrazine-6-carboxamide The expected product is obtained by separation of the racemic mixture obtained in the above Step on a chiral HPLC column.
Elemental microanalysis:

|  | % C | % H | % N |
|---|---|---|---|
| Calculated: | 57.52 | 4.39 | 15.24 |
| Found: | 57.73 | 4.61 | 15.05 |

EXAMPLE 26

(6S)-3-{[2,2-Difluoro-2-(1-oxido-3-pyridyl)ethyl]amino}-N-(2-fluorobenzyl)-4-oxo-4,6,7,8-tetrahydropyrrolo[1,2-a]pyrazine-6-carboxamide The expected product is obtained according to the procedure of Example 25, with the replacement of 2,2-difluoro-2-(1-oxido-4-pyridyl)ethanamine with 2,2-difluoro-2-(1-oxido-3-pyridyl)ethanamine in Step A.
Elemental microanalysis:

|  | % C | % H | % N |
|---|---|---|---|
| Calculated: | 57.52 | 4.39 | 15.24 |
| Found: | 57.34 | 4.49 | 14.99 |

EXAMPLE 27

3-{[2,2-Difluoro-2-(1-oxido-2-pyridyl)ethyl]amino}-8,8-dimethyl-N-(2-fluorobenzyl)₄-oxo-4,6,7,8-tetrahydropyrrolo[1,2-a]pyrazine-6-carboxamide The expected product is obtained according to the procedure of Example 1, with the replacement of benzyl 5-oxoprolinate with benzyl 4,4-dimethyl-5-oxo-2-pyrrolidinecarboxylate in Step A.

EXAMPLE 28

(6R)-3-{[2,2-Difluoro-2-(1-oxido-2-pyridyl)ethyl]amino}-8,8-dimethyl-N-(2-fluorobenzyl)-4-oxo-4,6,7,8-tetrahydropyrrolo[1,2-a]pyrazine-6-carboxamide The racemic mixture of Example 27 is separated by chiral phase preparative HPLC chromatography.
The expected product is the first of the enantiomers so obtained.
Elemental microanalysis:

|  | % C | % H | % N |
|---|---|---|---|
| Calculated: | 59.13 | 4.96 | 14.37 |
| Found: | 58.88 | 4.99 | 14.08 |

EXAMPLE 29

(6S)-3-{[2,2-Difluoro-2-(1-oxido-2-pyridyl)ethyl]amino}-8,8-dimethyl-N-(2-fluorobenzyl)₄-oxo-4,6,7,8-tetrahydropyrrolo[1,2-a]pyrazine-6-carboxamide The racemic mixture of Example 27 is separated by chiral phase preparative HPLC chromatography.
The expected product is the second of the enantiomers so obtained.
Elemental microanalysis:

|  | % C | % H | % N |
|---|---|---|---|
| Calculated: | 59.13 | 4.96 | 14.37 |
| Found: | 58.92 | 4.93 | 14.14 |

EXAMPLE 30

(6S)-3-{[2,2-Difluoro-2-(1-oxido-2-pyridyl)ethyl]amino}-4-oxo-N-[(5-oxo-4,5-dihydro-1H-1,2,4-triazol-3-yl)methyl]-4,6,7,8-tetrahydropyrrolo[1,2-a]pyrazine-6-carboxamide Step A: 3-{[2,2-Difluoro-2-(1-oxido-2-pyridyl)ethyl]amino}-4-oxo-N-[(5-oxo-4,5-dihydro-1H-1,2,4-triazol-3-yl)methyl]-4,6,7,8-tetrahydropyrrolo[1,2-a]pyrazine-6-carboxamide The expected product is obtained according to the procedure described in Example 1, with the replacement of 2-fluorobenzylamine with 5-(aminomethyl)-2,4-dihydro-3H-1,2,4-triazol-3-one in Step L.

Step B: (6S)-3-{[2,2-Difluoro-2-(1-oxido-2-pyridyl)ethyl]amino}-4-oxo-N-[(5-oxo-4,5-dihydro-1H-1, Z 4-triazol-3-yl)methyl]-4,6,7,8-tetrahydropyrrolo[1,2-a]pyrazine-6-carboxamide The expected product is obtained by separation of the racemic mixture obtained in the above Step on a chiral HPLC column.
Elemental microanalysis:

|  | % C | % H | % N |
|---|---|---|---|
| Calculated: | 48.22 | 4.05 | 24.99 |
| Found: | 48.61 | 4.34 | 24.56 |

EXAMPLE 31

(6S)-3-{[2,2-Difluoro-2-(1-oxido 2-quinolinyl)ethyl]amino}-N-(2-fluorobenzyl)₄-oxo-4,6,7,8-tetrahydropyrrolo[1,2-a]pyrazine 6-carboxamide Step A: 3-{[2,2-Difluoro-2-(1-oxido-2-quinolinyl)ethyl]amino}-N-(2-fluorobenzyl)-4-oxo-4,6,7,8-tetrahydropyrrolo[1,2-a]pyrazine-6-carboxamide The expected product is obtained according to the procedure described in Example 1, with the replacement of 2,2- difluoro-2-(1-oxido-2-pyridyl)ethanamine with 2,2-difluoro-2-(1-oxido-2-quinolinyl)ethanamine in Step J.

Step B: (6S)-3-{[2,2-Difluoro-2-(1-oxido-2-quinolinyl)ethyl]amino}-N-(2-fluorobenzyl)-4-oxo-4,6,7,8-tetrahydropyrrolo[1,2-a]pyrazine-6-carboxamide The expected product is obtained by separation of the racemic mixture obtained in the above Step on a chiral HPLC column.

Elemental microanalysis:

|  | % C | % H | % N |
|---|---|---|---|
| Calculated: | 61.29 | 4.35 | 13.75 |
| Found: | 61.65 | 4.51 | 13.50 |

Pharmacological Study of the Compounds of the Invention

EXAMPLE 32

Inhibition of Thrombin and of Fibrinolysis Serine Proteases

For in vitro evaluation of the inhibitory activity of the products of the invention on human thrombin (Sigma, specific activity 3230 UNIH/mg), purified human fibrinogen (4 mM, Stago) (Fg) was added to a given amount of thrombin (0.7 nM) that had previously been incubated with or without the inhibitor to be tested (20° C., 10 minutes).

Inhibitors, enzymes and substrates are diluted in the same buffer (0.01 mM phosphate buffer, pH 7.4, containing 0.12 M sodium chloride and 0.05% bovine serum albumin) and then distributed on a polystyrene microtitre plate in a volume of 50 µl.

The fibrin formed by the thrombin is measured using a spectrophotometer at 405 nm after from 10 to 15 minutes' reaction at 20° C.

The table below gives in nM the concentration of the compounds that inhibits 50% of the enzymatic activity ($IC_{50}$) of the thrombin compared with the control without product. The results obtained show that the compounds of the invention are potent inhibitors of the activity of human thrombin on human fibrinogen.

TABLE

| Example | $IC_{50}$ (nM) |
|---|---|
| 1 | 28 |
| 3 | 16 |
| 8 | 38 |
| 15 | 1.4 |
| 21 | 11 |
| 24 | 60 |
| 31 | 8.4 |

EXAMPLE 33

Pharmaceutical Composition

Formulation for the preparation of 1000 tablets each containing a dose of 10 mg:

| compound of Example 3 | 10 g |
|---|---|
| hydroxypropyl cellulose | 2 g |
| wheat starch | 10 g |
| lactose | 100 g |
| magnesium stearate | 3 g |
| talc | 3 g |

We claim:

1. A compound of formula (I):

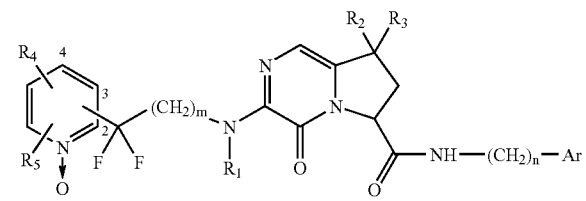

wherein:

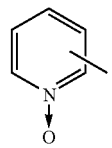

represents 1-oxidopyridyl substituted by the remainder of the molecule in any one of the positions 2, 3 and 4, m and n, which are identical or different, each represent an integer of from 1 to 3, $R_1$ represents hydrogen or linear or branched ($C_1$-$C_6$)alkyl, $R_2$ and $R_3$, which may be identical or different, each represent an atom or group selected from hydrogen, halogen, linear or branched ($C_1$-$C_6$)alkyl, hydroxy, linear or branched ($C_1$-$C_6$)acyloxy and linear or branched ($C_1$-$C_6$)alkoxy, or, together with the carbon atom carrying them, form a cycloalkane having from 3 to 6 carbon atoms, $R_4$ and $R_5$ each represent hydrogen, or are adjacent and, together with the carbon atoms carrying them, form a benzo ring, Ar represents aryl or heteroaryl, or enantiomers, or an addition salt thereof with a pharmaceutically acceptable acid, it being understood that:

"aryl" is phenyl, optionally substituted by one or more identical or different groups selected from:

halogen, linear or branched ($C_1$-$C_6$)alkoxy, hydroxy, carboxymethoxy, and carbamoylmethoxy optionally N-substituted by one or two groups selected from linear or branched ($C_1$-$C_6$)alkyl, hydroxy-($C_1$-$C_6$)alkyl in which the alkyl moiety may be linear or branched, alkoxyalkyl in which the alkoxy and alkyl moieties are each linear or branched $C_1$-$C_6$, and pyridylalkyl in which the alkyl moiety is linear or branched $C_1$-$C_6$, and "heteroaryl" is thienyl or triazolyl optionally substituted by oxo.

2. A compound of claim 1, wherein the configuration of the asymmetric centre at the alpha position with respect to the amide is (S).

3. A compound of claim 1, wherein m is 1, or enantiomers or an addition salt with a pharmaceutically acceptable acid.

4. A compound of claim 1, wherein n is 1, or enantiomers or an addition salt with a pharmaceutically acceptable acid.

5. A compound of claim 1, wherein $R_1$ represents hydrogen, or enantiomers, or an addition salt with a pharmaceutically acceptable acid.

6. A compound of claim 1, wherein $R_2$ and/or $R_3$ represents hydrogen, or enantiomers, or an addition salt with a pharmaceutically acceptable acid.

7. A compound of claim 1, wherein $R_4$ and $R_5$ each represent hydrogen, or enantiomers, or an addition salt with a pharmaceutically acceptable acid.

8. A compound of claim 1, wherein $R_4$ and $R_5$ are adjacent and, together with the carbon atoms carrying them, form a benzo ring, or enantiomers or an addition salt with a pharmaceutically acceptable acid.

9. A compound of claim 1, wherein Ar represents phenyl unsubstituted or substituted by one or more identical or different halogen selected from fluorine and chlorine, or enantiomers, or an addition salt with a pharmaceutically acceptable acid.

10. A compound of claim 1 selected from:
3-{[2,2-difluoro-2-(1-oxido-2-pyridyl)ethyl]amino}-N-(2-fluorobenzyl)-4-oxo-4,6,7,8-tetrahydropyrrolo[1,2-a]pyrazine-6-carboxamide, or the (6S) enantiomer,
3-{[2,2-difluoro-2-(1-o xido-2-pyridyl)ethyl]amino}-N-(2,6-difluorobenzyl)-4-oxo-4,6,7,8-tetrahydropyrrolo[1,2-a]pyrazine-6-carboxamide, or the (6S) enantiomer,
3-{[2,2-difluoro-2-(1-oxido-2-pyridyl)ethyl]amino}-N-(2-chlorobenzyl)-4-oxo-4,6,7,8-tetrahydropyrrolo[1,2-a]pyrazine-6-carboxamide, or the (6S) enantiomer;
3-{[2,2-difluoro-2-(1-oxido-2-pyridyl)ethyl]amino}-N-(2,5-difluorobenzyl)-4-oxo-4,6,7,8-tetrahydropyrrolo[1,2-a]pyrazine-6-carboxamide, or the (6S) enantiomer,
3-{[2,2-difluoro-2-(1-oxido-2-pyridyl)ethyl]amino}-N-(2,3-difluorobenzyl)-4-oxo-4,6,7,8-tetrahydropyrrolo[1,2-a]pyrazine-6-carboxamide, or the (6S) enantiomer, and 3-{[2,2-difluoro-2-(1-oxido-2-pyridyl)ethyl]amino}-N-(2,3,6-trifluorobenzyl)-4-oxo-4,6,7,8-tetrahydropyrrolo[1,2-a]pyrazine-6-carboxamide, or the (6S) enantiomer.

11. A pharmaceutical composition comprising as active ingredient a compound of claim 1 in combination with one or more pharmaceutically acceptable, inert, non-toxic carriers.

12. A method of treating a living animal body, including a human, afflicted with a condition selected from myocardial infarction and venous or arterial thromboses comprising the step of administering to the living animal body, including a human, an effective amount of a compound of claim 1.

* * * * *

UNITED STATES PATENT AND TRADEMARK OFFICE
CERTIFICATE OF CORRECTION

PATENT NO. : 7,498,330 B2  
APPLICATION NO. : 11/079638  
DATED : March 3, 2009  
INVENTOR(S) : Guillaume DeNanteuil et al.

Page 1 of 1

It is certified that error appears in the above-identified patent and that said Letters Patent is hereby corrected as shown below:

Cover Page, item (73), Assignee: "Les Laboratories Servier" should be -- Les Laboratoires Servier --.

Column 20, Line 45: "may be" should be -- are --.

Column 22, Line 5: "1-o xido" should be -- 1-oxido --.

Signed and Sealed this

Thirtieth Day of March, 2010

David J. Kappos
*Director of the United States Patent and Trademark Office*